United States Patent [19]

Hermanson

[11] Patent Number: 5,304,673

[45] Date of Patent: Apr. 19, 1994

[54] PROCESS FOR RECOVERING DIMETHYL TEREPHTHALATE AND ETHYLENE GLYCOL

[75] Inventor: Paul M. Hermanson, Oak Lawn, Ill.

[73] Assignee: Enviropur Waste Refining And Technology, Inc., McCook, Ill.

[21] Appl. No.: 11,411

[22] Filed: Jan. 29, 1993

[51] Int. Cl.⁵ .................... C07C 67/62; C07C 27/26
[52] U.S. Cl. .................... 560/78; 568/868; 568/871
[58] Field of Search ................. 560/78; 568/868, 871

[56] References Cited

U.S. PATENT DOCUMENTS

| | | | |
|---|---|---|---|
| 4,066,835 | 1/1978 | Hahn et al. | 560/98 |
| 4,076,946 | 2/1978 | Millick | 560/78 |
| 4,241,216 | 12/1980 | Bergman et al. | 560/99 |
| 4,929,749 | 5/1990 | Gupta et al. | 560/79 |
| 5,051,528 | 9/1991 | Naujokas et al. | 560/78 |

*Primary Examiner*—Jose G. Dees
*Assistant Examiner*—Vera C. Clarke
*Attorney, Agent, or Firm*—Dressler, Goldsmith, Shore, Milnamow, ltd.

[57] ABSTRACT

A process for recovering dimethyl terephthalate and ethylene glycol from a stream including aqueous ethylene glycol is described. Adding a dispersing agent to the stream renders it filterable, and a subsequent cooling of the stream containing the dispersing agent causes dimethyl terephthalate to precipitate in a form which can be removed by conventional filtration. The precipitated dimethyl terephthalate is of a quality and purity suitable for use in the manufacture of polyethylene terephthalate. A commercially valuable ethylene glycol stream is also recovered by the process.

11 Claims, 2 Drawing Sheets

PROCESS FOR RECOVERING DIMETHYL TEREPHTHALATE AND ETHYLENE GLYCOL

TECHNICAL FIELD

The invention relates to a method for recovering dimethyl terephthalate and ethylene glycol from an aqueous ethylene glycol stream. More specifically, the invention relates to precipitating dimethyl terephthalate particles from an industrial waste by-product stream.

BACKGROUND OF THE INVENTION

Dimethyl terephthalate is widely utilized in the manufacture of polyethylene terephthalate, a plastic utilized in plastic beverage containers, Dacron TM clothing material and other commercial products. In the manufacturing process, dimethyl terephthalate typically is mixed with ethylene glycol and brought into contact with an acidic catalyst, such as an oxide of antimony. A substantial portion of the dimethyl terephthalate reacts with the ethylene glycol to produce polyethylene terephthalate, methanol, and water. Some intermediate polymers, such as oligomers of dimethyl terephthalate are also produced.

Polyethylene terephthalate and other relatively volatile components are recovered by distillation in a resin tower. As a by-product, the distillation produces a bottoms stream which includes unreacted dimethyl terephthalate, relatively low molecular weight dimethyl terephthalate oligomers, ethylene glycol, and water. Additionally, the bottoms stream often contains a small amount of residual polyethylene terephthalate, traces of the acidic catalyst, and insoluble contaminants. Corrosion products and relatively high molecular weight polymers produced by heat degradation are examples of such insoluble contaminants.

Previously, unreacted dimethyl terephthalate which entered the bottoms stream has been considered unrecoverable. The bottoms stream is not susceptible to conventional filtration because the mixture of dimethyl terephthalate, ethylene glycol, and water quickly fouls conventional filters. Somewhat longer filter runs can be obtained by a filter precoat, such as a coating of diatomaceous earth, on the conventional filters, but such precoats tend to become mixed with the filter cake. Additionally, conventional filtration yields a filter cake of dimethyl terephthalate that is contaminated by catalyst, corrosion products, and thermal degradation polymer products.

Upon leaving the resin tower, the bottoms stream is usually subjected to one or more distillation steps which reclaims ethylene glycol for recycling. Unfortunately, as the level of ethylene glycol in the bottoms stream is reduced, the dimethyl terephthalate and its oligomers become increasingly heat sensitive. Distilling the bottoms stream to about 10% to about 15% ethylene glycol content by volume thermally degrades polymers present in the stream to such an extent that the stream exhibits a viscosity similar to modeling clay.

Consequently, the residual bottoms stream has long been considered worthless. For example, the stream is sometimes incinerated as hazardous waste or placed in landfills.

A need exists for a practical method of separating dimethyl terephthalate and its oligomers from aqueous ethylene glycol streams. Such a recovery process would not only produce valuable dimethyl terephthalate for use in plastic manufacturing, but would also prevent unnecessary filling of increasingly scarce landfills. Additionally, petroleum reserves which are presently consumed to replace the dimethyl terephthalate that is lost could be conserved if such a method were practiced.

SUMMARY OF THE INVENTION

The invention is a process for recovering dimethyl terephthalate from an aqueous ethylene glycol stream. A dispersing agent reduces the viscosity of the stream, disperses dimethyl terephthalate and polyethylene terephthalate, and makes filtration of the stream commercially practical. Cooling the stream containing the dispersing agent causes dimethyl terephthalate to precipitate in the form of solid particles which can be recovered by filtration. The recovered dimethyl terephthalate is sufficiently pure to be utilized as a charge material for the production of polyethylene terephthalate plastics. Herein, a material that is suitable for immediate use as a charge stock for a polyethylene terephthalate manufacturing unit, and which contains at least about 60 wt. % of dimethyl terephthalate will be called "substantially pure dimethyl terephthalate". The process also produces a relatively pure ethylene glycol stream of commercial value.

In one aspect, the invention is a process for separating substantially pure dimethyl terephthalate from an aqueous stream. The aqueous stream contains dimethyl terephthalate, ethylene glycol, and water. The stream may additionally contain oligomers of dimethyl terephthalate, polyethylene terephthalate, and residual catalyst from other processes. The stream may also contain contaminants such as thermally degraded polymers and ferrous corrosion products.

In this aspect, the process comprises the steps of adding a dispersing agent to the stream in an amount effective to produce a pH in the range of about 8.5 to about 9.5. The effective amount tends to disperse the dimethyl terephthalate, but does not render the dimethyl terephthalate immune to a subsequent thermally-induced precipitation.

Thereafter, the stream is cooled sufficiently to precipitate particulate dimethyl terephthalate. The particulate is recovered by filtration, yielding a filter cake comprising dimethyl terephthalate in substantially pure form. The recovery of the particulate produces a filtrate that is rich in ethylene glycol. The filtrate may be further purified by distillation.

When thermally degraded polymers of relatively high molecular weight or ferrous corrosion products are present in the aqueous stream in objectionable amounts, they are removed by filtration after the dispensing agent been added to the aqueous stream. Surprisingly, the dispersing agent permits a substantial amount of the dimethyl terephthalate to pass through a conventional filter. An overall decrease in viscosity of the aqueous stream often accompanies the addition of the dispersing agent.

In another aspect, the process comprises adding a diamine to the aqueous stream that contains dimethyl terephthalate, ethylene glycol, and water. The diamine is of the formula:

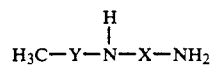

wherein Y is $[(CH_2)_n(C=C)_p]_r(CH_2)_m$ where m and n are independently 1 to 13, p is 1 to 3 and r is 1 to 3; and X is $(CH_2)_y$ where y is 2 to 4. After the diamine is added, the aqueous stream is cooled sufficiently to precipitate particulate dimethyl terephthalate. The particulate is separated by filtration to produce two commercially valuable product streams. One of the streams contains substantially pure dimethyl terephthalate and the other is enriched in ethylene glycol.

DETAILED DESCRIPTION OF THE INVENTION

The invention can be practiced with any feed stream that contains dimethyl terephthalate, ethylene glycol, and water. Alternatively, the invention can be practiced with initially dry streams containing dimethyl terephthalate to which water is subsequently added. Preferably, the feed stream is a by-product produced in the course of manufacturing polyethylene terephthalate (hereinafter referred to as "PET"). For example, the feed stream may be a bottoms stream from the resin tower of a PET manufacturing unit. Alternatively, the feed stream can be a residual bottoms stream produced by evaporating or distilling a bottoms stream. The feed stream can be waste material produced in the course of cleaning a PET reactor. In each of these cases, the feed stream may contain oligomers of dimethylene terephthalate, catalysts, and ferrous corrosion products.

Figure 1:
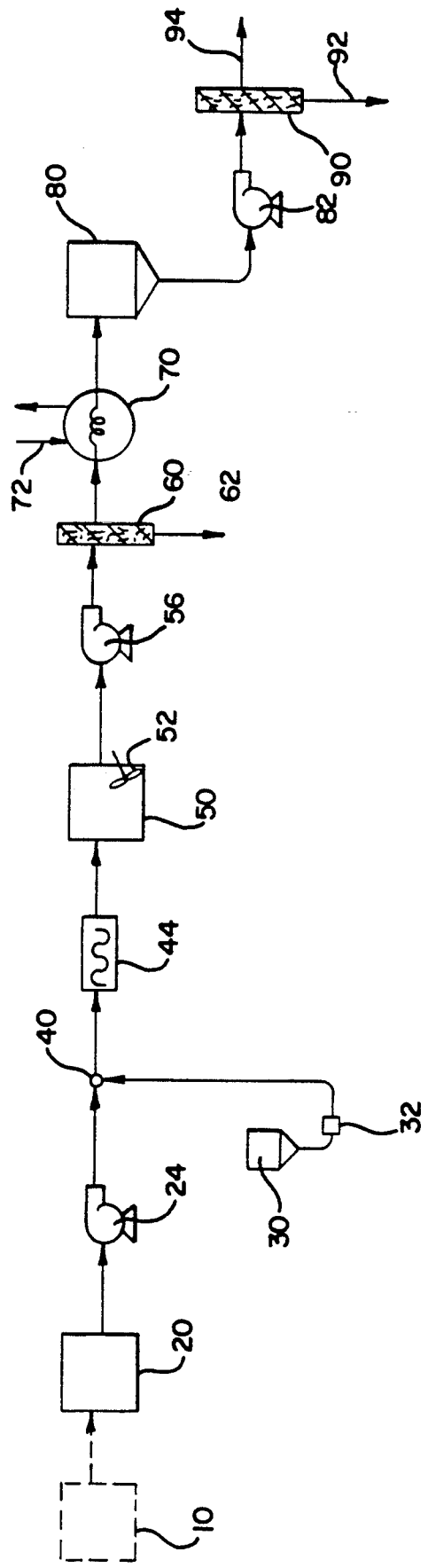
FIG. 1 shows a process flow diagram of a separation process in accordance with the present invention.

A flow diagram for a process in accordance with the present invention is shown in FIG. 1. A pumpable feed stream is conveniently accumulated in a feed storage tank 20. Preferably, the feed stream is produced by an upstream PET manufacturing unit 10, which is not part of the present invention. If the feed stock to be recovered is not received in pumpable form, additional solvent material such as water or ethylene glycol may be added to achieve a pumpable viscosity. Typically, the pumpable material in the feed storage tank 20 will be acidic and have a pH in the range of about 2 to about 5. In many cases, this relatively acidic pH range is caused by the presence of residual amounts of a catalyst, such as antimony oxide, which is present in the feed stock in trace amounts. A typical feed stock contains antimony oxide in amounts of about 1,000 parts per million by weight. Feed storage tank 20 is preferably maintained at atmospheric pressure.

The feed stock in storage tank 20 can be in the form of a clear solution or, alternatively, can have up to about 50% by weight solids. Preferably, the feed will not have been distilled, for example, to reclaim ethylene glycol, and contains about 0% to about 10% by weight solids, most preferably about 5% by weight solids. The solid material is substantially dimethyl terephthalate but includes dimethyl terephthalate oligomers and polyethylene terephthalate. The slurry is withdrawn from the storage tank 20 by a feed transfer pump 24 and is directed to addition point 40.

A dispersing agent is provided in tank 30. Metering pump 32 meters the dispersing agent at a controlled rate and delivers the dispersing agent to addition junction 40. Optionally, an in-line mixer, such as static mixer 44, is employed downstream of the junction 40 to ensure intimate contact between the feed stream and the dispersing agent. Alternatively, centrifugal pumps may be employed as mixers. The feed stream containing the dispersing agent enters a reaction vessel 50.

The rate of the chemical metering pump 32 is controlled relative to the rate of the feed stream through the feed transfer pump 24 as necessary to adjust the pH of the feed stream in the range of about 8.5 to about 9.5. Preferably, the proportion of dispersing agent in the feed stream is sufficient to substantially disperse the dimethyl terephthalate present in the stream, so as to permit a substantial portion of the dimethyl terephthalate present to pass through a conventional filter.

In cases where thermal degraded polymers are present, such as in residual bottoms stream which have been partially reclaimed by distillation, adjusting the pH to the range of about 8.5 to about 9.5 by adding the dispersing agent is accompanied by a dramatic decrease in the viscosity of the combined stream, as compared to the viscosity of the untreated feed stream.

It has been observed that when the pH of the feed stream is below about 8, an appreciable amount of the dimethyl terephthalate is generally not dispersed. Conversely, when the pH of the combined feed is adjusted to more than about 9.5, the subsequent precipitation of dimethyl terephthalate (described below) is impaired. Therefore, an effective amount of dispersing agent is one that adjusts the pH to the specified range, and disperses dimethyl terephthalate without preventing subsequent thermally-induced precipitation of dimethyl terephthalate.

The composition and dosage of the dispersing agent is chosen to achieve an optimum level of dispersion for dimethyl terephthalate and its oligomers, consistent with efficient subsequent precipitation of the dimethyl terephthalate. Preferably, the dispersing agent composition also provides a decrease in feed stream viscosity which enhances filterability of the feed stream. The dispersing agent optionally serves as a flocculant for insoluble contaminants such as iron corrosion products. The dispersing agent should be miscible in the feed stream and have a vapor pressure and flash point commensurate with use at atmospheric pressure in open tanks.

Preferred dispersing agents contain a diamine compound having a linear or branched hydrocarbon group attached to one of its nitrogen atoms. The group should be substantially lipophilic in nature. The exact length and make-up of the group is tailored to the specific feed stream composition with which the dispersing agent is to be combined. Preferably, the group will have approximately 12 to about 20 carbon atoms. Most preferably, the group has a linear structure. The linear structure of the group may be aliphatic or it may contain 1, 2 or 3 olefinic carbon-to-carbon bonds.

The diamine portion of the dispersing agent is hydrophilic and, preferably, contains 2, 3 or 4 carbon atoms. It is especially preferred that the diamine portion of the dispersing agent be aliphatic in nature.

The diamine is generally a compound of the formula:

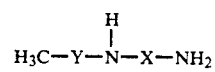

wherein Y is $[(CH_2)_n(C=C)_p]_r(CH_2)_m$ where m and n are independently 1 to 13, p is 1 to 3 and r is 1 to 3; and X is $(CH_2)_y$ where y is 2 to 4.

Preferably the diamine is a compound of the formula:

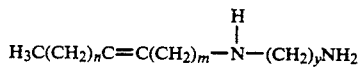

$$H_3C(CH_2)_nC=C(CH_2)_m-\overset{H}{\underset{|}{N}}-(CH_2)_yNH_2$$

where m and n are independently 3 to 10 and y is 2 to 4.

Good results have been obtained employing N-oleyl-1,3-diaminopropane. This compound is commercially available from Akzo Corporation, of Illinois, under the tradename Duomeen O ™.

The dispersing agent is preferably injected at a rate which results in a concentration in the range of about 0.1 to about 0.2 volume percent of the stream. Addition of an effective amount of the dispersing agent adjusts the pH to in the range of about 8.5 to 9.5.

If more than the effective amount of the dispersing agent is added to the feed stream, a relatively large temperature decrease is required to precipitate the particulate dimethyl terephthalate. A decrease in temperature alone can be insufficient to produce precipitation when an excessive amount of the dispersing agent is added. In those cases, precipitation can be induced by decreasing the pH, for example, by addition of oleic acid. However, the precipitate that is produced by increasing the pH is different in appearance from the precipitate induced thermally, being longer and stringier, and often tends to foul conventional filter media.

The stream is sent to a reaction tank 50 which affords additional residence time so that the combined stream approaches an equilibrium dispersion. The reaction tank 50 includes a propeller mixer 52, to agitate the contents of the reaction tank and hasten the approach to the equilibrium dispersion. A feed transfer pump 56 transports the stream from the reaction tank 50 to an optional filter 60.

The filter 60 is desirable in cases where the feed stream is known to contain a relatively high level of insoluble contaminants, such as iron corrosion products and relatively high molecular weight polymer degradation products. It is recommended that a bench scale test be conducted to determine whether the filter 60 should be employed. In the bench test, samples of the feed stream are mixed with incremental amounts of dispersing agent until a PH of about 10 is achieved. If visual inspection reveals any solid particles remaining in the bench test mixture at pH 10, utilization of the optional filter 60 is recommended. Generally, residual bottoms streams which have been partially reclaimed by distillation are good candidates for the filter 60.

The filter 60 can be any conventional type of filter. For example, the filter 60 may be a plate and frame filter or a rotary vacuum filter with scraper. Additionally, the filter 60 may be replaced by separation means such as a centrifuge or a cyclone separator. Herein, conventional filtration is considered to include such well-known and widely-employed separation means.

Insoluble contaminants are retained by the filter and removed from the process. The removed contaminants 62 can sometimes be used as a charge stock for producing dark colored plastics. Alternatively, the insoluble contaminants 62 may be sent to disposal. Surprisingly, the present invention disperses the dimethyl terephthalate in the combined stream so thoroughly that a substantial portion, preferably all, of the dimethyl terephthalate passes through the filter 60 and is delivered to a heat exchanger 70.

The function of the heat exchanger is to cool the combined stream. The heat exchanger 70 produces a decrease in the temperature of the stream which causes particles of dimethyl terephthalate to precipitate in particulate form. The heat exchanger 70 should cool the stream at least about 10° F. below the temperature of the reaction tank. Generally, it is believed that greater cooling will produce higher recoveries of particulate dimethyl terephthalate. However, it is not intended that the stream be cooled to a temperature which causes a substantial portion of the ethylene glycol to freeze.

The heat exchanger 70 may be cooled by a cooling stream 72, such as cooling water, or a refrigerant such as freon. It is recommended that the stream be on the tube side of a shell and tube exchanger.

After traveling through the heat exchanger 70, the feed stream is sent to a precipitation vessel 80 which holds the stream in a relatively quiescent state for a sufficient time to permit the particles of dimethyl terephthalate to form. The precipitation vessel preferably provides a residence time of at least 0.1 hour, more preferably at least 1 hour. The particles, being heavier than the surrounding aqueous ethylene glycol liquid tend to sink.

It is recommended that the precipitation vessel 80 have a cone-shaped bottom to facilitate withdrawal of the particulate. Preferably, both the aqueous ethylene glycol liquid and the particulate are withdrawn together and pass to a precipitate transfer pump 82.

At the discharge of the precipitate transfer pump 82 is a product filter 90. The filter 90 is a conventional filter, selected from conventional filters intended for removing relatively large volumes of particulate. For example, the filter 90 may be a plate and frame filter, a leaf filter, or a rotary vacuum filter with wiper blades. Conventional separating means, such as cyclone separators, can optionally be utilized to accomplish the function of the filter 90.

Commercially valuable ethylene glycol preferably leaves the product filter 90 as a glycol stream 94. Subsequently, the glycol stream 94 can be distilled to produce an ethylene glycol stream, an azeotrope stream, and a water stream. The ethylene glycol and diethylene glycol so recovered are commercially valuable and can be reused in plastic manufacturing processes, in anti-freeze, and for other uses.

The filter cake obtained from product filter 90 constitutes a particulate product stream 92 which is dried, as by exposure to a relatively dry gas stream, to produce a powdery substance rich in dimethyl terephthalate and its oligomers. Additionally, some small amount of polyethylene terephthalate may also be present in the stream 92. In most cases, only a negligible amount of the dispersing agent is present in the particulate product stream 92, and the level can be reduced by subsequent washing steps. Some liquid water or ice may be precipitated with the particulate dimethyl terephthalate. Preferably, particulate product stream 92 will be substantially composed of dimethyl terephthalate of a purity and quality that make it suitable for immediate use, for example, in the manufacture of polyethylene terephthalate.

The following example is provided to further communicate the invention. The example does not limit the scope of the invention in any way.

EXAMPLE 1

An experiment was performed utilizing a sample of a resin tower residual bottoms stream that was produced within a commercial polyethylene terephthalate manufacturing unit. The residual bottoms stream had been produced at the manufacturing plant by distilling a resin tower bottoms stream in order to reclaim a portion of the ethylene glycol and the diethylene glycol present in the resin tower bottoms stream.

The sample was analyzed by gas-liquid chromatography and was found to contain 52.1% by weight ethylene glycol and 2.2% by weight diethylene glycol. Additionally, a water analysis in accordance with the well-known Karl-Fisher method indicated that the sample contained 10.2% by weight water. By difference, it was inferred that a balance portion of this sample, characterized as not glycol and not water, represented 35.0 weight percent of the total. Based on experience with similar previous samples, it is believed that a large part of the balance portion was constituted by dimethylene terephthalate and oligomers. The specific gravity of the total sample was determined to be 1.1761, with respect to water at 60° F.

500 milliliters of the sample was placed in a 1,000 milliliter beaker and stirred with a spatula at room temperature. A magnetic stirring bar was also placed in the beaker, but the sample proved to be so viscous that the magnetic stirrer bar did not turn at all under the influence of its magnetic driver and, therefore, stirring by spatula was necessary.

The pH of the sample was observed to be about 2.5 as indicated by both pH paper and an electronic pH meter. A dispersing agent was added incrementally to the beaker, a thorough stirring by spatula and a pH measurement were performed after each dispersing agent addition. The dispersing agent was Duomeen O TM, which is commercially available from the Akzo Corporation of Illinois. The results of the pH determination are presented below in Table 1.

TABLE 1

| Cumulative Volume of Dispersing Agent in Mixture (ml) | pH of Mixture After Addition |
| --- | --- |
| 0.0 | 2.5 |
| 0.1 | 3.0 |
| 0.2 | 5.0 |
| 0.3 | 6.0 |
| 0.4 | 7.0 |
| 0.5 | 7.5 |
| 0.6 | 8.5 |
| 0.65 | 9.5 |

It was observed that when the pH of the mixture approached 8.5, the viscosity of the mixture decreased dramatically. In fact, at pH 8.5 and above it was possible to utilize the magnetic stirring bar, and it was no longer necessary to stir the mixture by spatula as at lower pH.

At 9.5 pH the stirring bar was used to agitate the mixture for approximately 20 minutes. Then, the mixture was transferred to a Buchner funnel containing a paper filter and connected via a filter seal to a side arm flask and a vacuum pump. In this manner, the mixture was vacuum filtered. A filter cake was obtained weighing 17.4 grams.

The filter cake represented 2.89% of the original weight of the 500 ml sample, neglecting the weight of dispersing agent. Based on experience with similar, previous samples of resin tower residual bottoms streams obtained from the same manufacturer, it is believed that the filter cake was predominantly composed of relatively insoluble contaminants, such as ferrous corrosion products and thermally degraded high molecular weight polymers. Accordingly, the filter cake was merely inspected, weighed, and discarded.

The filtrate was a brown, transparent liquid having an appearance similar to iced tea. The filtrate was cooled from a room temperature of 71° F. to a final temperature of 55° F. Cooling caused the previously transparent filtrate to take on a milky appearance. Simultaneously, it was observed that the viscosity of the filtrate increased significantly.

Figure 2:
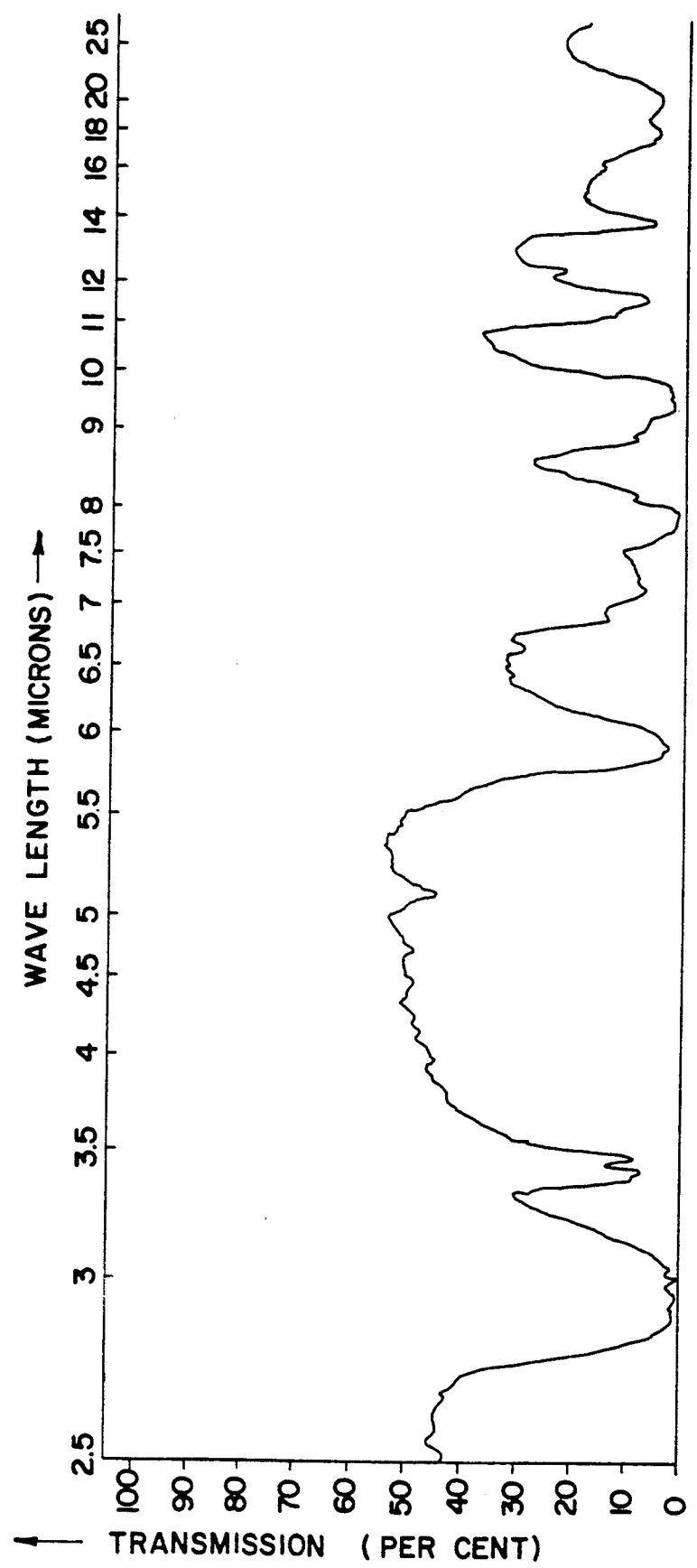
FIG. 2 depicts a trace of energy transmission as a function of wavelength for a sample of material recovered using the present invention.

The cooled filtrate was subjected to a second vacuum filtering step, using apparatus identical to that described above. After the second vacuum filtration ceased to produce filtrate, the vacuum pump was kept running and continued to draw air across the filter cake for an additional 35 minutes. The passage of air dried the filter cake to produce a powdery substance. The filter cake weighed 171.4 grams, which represents 29.1% of the total weight of the original 500 ml sample, neglecting the weight of dispersing agent. The melting point of the filter cake was determined to be 138° C. The filter cake exhibited an infrared spectrum substantially similar to that known to be produced by pure dimethyl terephthalate. A trace of energy transmission as a function of wavelength, produced in the course of performing an infrared spectrum analysis on a portion of the filter cake, is presented in FIG. 2.

Based on experience with previous, similar residual resin tower bottom samples, it is believed that the second filter cake is composed of substantially pure dimethyl terephthalate. Accordingly, the yield of the second filter cake is deemed likely to be indicative of the yields and purities of dimethyl terephthalate which can be expected in commercial operation.

The filtrate from the second vacuum filtration step was also transparent, but it was colored a darker brown than the filtrate from the first filtration, described above. The second filtrate contained 84.1 weight percent ethylene glycol and diethylene glycol, as determined by gas-liquid chromatography analysis, and 14.6 weight percent water, measured by the Karl-Fisher technique. By mathematical difference, only 1.3 weight percent of the second filtrate was not glycol and not water.

Based on the results of this experiment, it is concluded that a partially distilled resin tower bottoms stream obtained from a commercial scale polyethylene terephthalate production unit contained 35.0 weight percent of material other than water and glycol. Of this unidentified material, more than about four-fifths passed through two consecutive paper filters via vacuum filtration and was recovered as a dry powdery material. The powdery material is believed to be substantially composed of dimethylene terephthalate and its oligomers.

The invention is communicated herein by description, hypotheses, examples, and figures. The description, examples, and figures do not limit the scope of the invention or the scope of the appended claims. The specification will undoubtedly suggest other, similar aspects of the invention to those skilled in the art. However, such aspects are within the scope of the invention.

Similarly, the success of the invention does not depend on the correctness of the hypotheses, which are presented only to better communicate the invention.

What is claimed is:

1. A process for separating substantially pure dimethyl terephthalate from an aqueous stream that contains dimethyl terephthalate and ethylene glycol, which comprises:

adding a diamine dispersing agent to an aqueous stream that contains dimethyl terephthalate and ethylene glycol in an amount effective to produce a pH in the range of about 8.5 to about 9.5;

cooling said aqueous stream sufficiently to precipitate particulate dimethyl terephthalate; and filtering said aqueous stream to recover said particulate dimethyl terephthalate.

2. The process of claim 1 wherein the dispersing agent is added in an amount in the range of about 0.1 to about 0.2 volume percent of the aqueous stream.

3. The process of claim 1 that further comprises the step of recovering the ethylene glycol.

4. The process of claim 1 wherein the initial pH of the untreated stream is in the range of about 2 to about 5.

5. The process of claim 1 wherein the viscosity of the aqueous charge stream is reduced by the addition of said dispersant.

6. The process of claim 1 wherein the diamine dispersing agent is a compound of the formula:

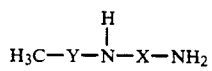

wherein Y is $[(CH_2)_n(C=C)_p]_r(CH_2)_m$
where m and n are independently 1 to 13, p is 1 to 3 and r is 1 to 3; and X is $(CH_2)_y$ where y is 2 to 4.

7. The process of claim 1 which further comprises the step of filtering said aqueous stream after adding said diamine dispersing agent.

8. A process for separating substantially pure dimethyl terephthalate from an aqueous stream that contains dimethyl terephthalate and ethylene glycol, which comprises:

adding a compound of the formula:

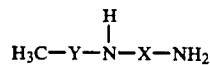

wherein Y is $[(CH_2)_n(C=C)_p]_r(CH_2)_M$
where m and n are independently 1 to 13, p is 1 to 3 and r is 1 to 3; and X is $(CH_2)_y$ where y is 2 to 4, in an amount effective to produce a pH in the range of about 8.5 to about 9.5.

9. The process of claim 8 wherein m and n are independently 3 to 10, p is 1, and y is 2 to 4.

10. A process for recovering dimethyl terephthalate from an aqueous slurry containing dimethyl terephthalate and ethylene glycol, which comprises adding sufficient N-oleyl-1,3-diaminopropane to an aqueous mixture containing dimethyl terephthalate and ethylene glycol to raise the pH of the mixture to a value in the range of about 8.5 to about 9.5;

cooling the mixture at least about 10° F., thereby precipitating dimethylene terephthalate particles; and recovering the dimethyl terephthalate particles by filtration.

11. The process of claim 10 that further comprises the step of recovering the ethylene glycol.

* * * * *